United States Patent [19]

Lustig

[11] 4,449,932

[45] May 22, 1984

[54] CONTRA-ANGLE HEAD FOR DENTISTRY

[76] Inventor: Leopold P. Lustig, 304 Greenwood St., Newton Center, Mass. 02159

[21] Appl. No.: 389,408

[22] Filed: Jun. 17, 1982

[51] Int. Cl.³ .......................... A61C 1/08; A61C 1/12
[52] U.S. Cl. ..................................... 433/126; 433/133
[58] Field of Search ................ 433/116, 126, 128, 133

[56] References Cited

U.S. PATENT DOCUMENTS

| | | | |
|---|---|---|---|
| 1,691,823 | 11/1928 | Ogilvie | 433/116 |
| 2,894,325 | 7/1959 | Flatland | 433/128 X |
| 4,053,983 | 10/1977 | Flatland | 433/133 |
| 4,268,252 | 5/1981 | Lustig | 433/133 X |
| 4,285,671 | 8/1981 | Lustig et al. | 433/133 X |

Primary Examiner—Robert P. Swiatek
Attorney, Agent, or Firm—Alfred H. Rosen

[57] ABSTRACT

A rigid tubular housing having a shaft alley and transverse to it at one end a dental tool chamber, has a telescopically-fitted cover which in one position gives access to the tool chamber via diametrically-opposed apertures one of which is always open and the other of which moves to open and close an access opening to the tool chamber. Locks for the cover fill both openings when the cover is closed over the access opening, as when a tool is in place in the chamber.

7 Claims, 11 Drawing Figures

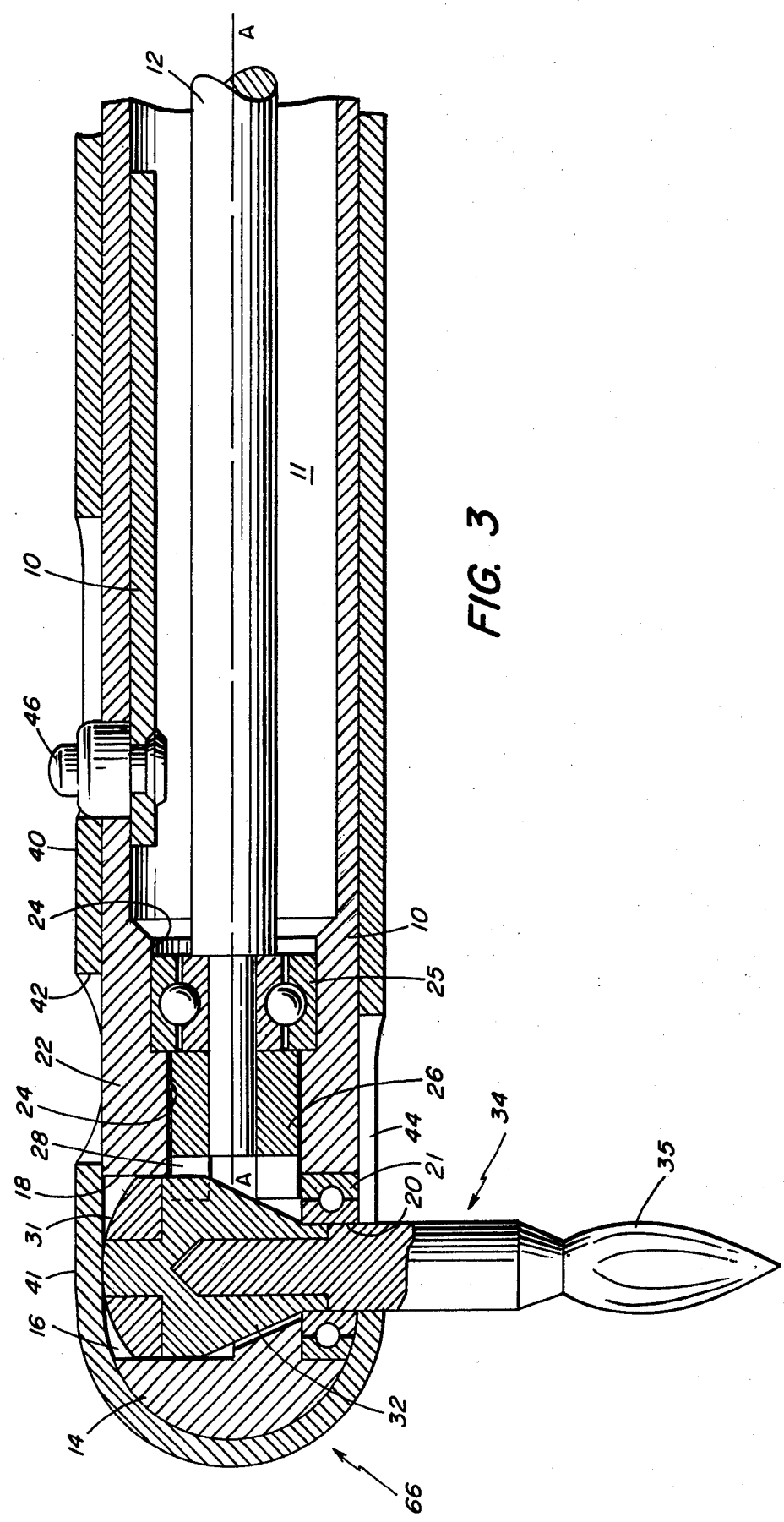

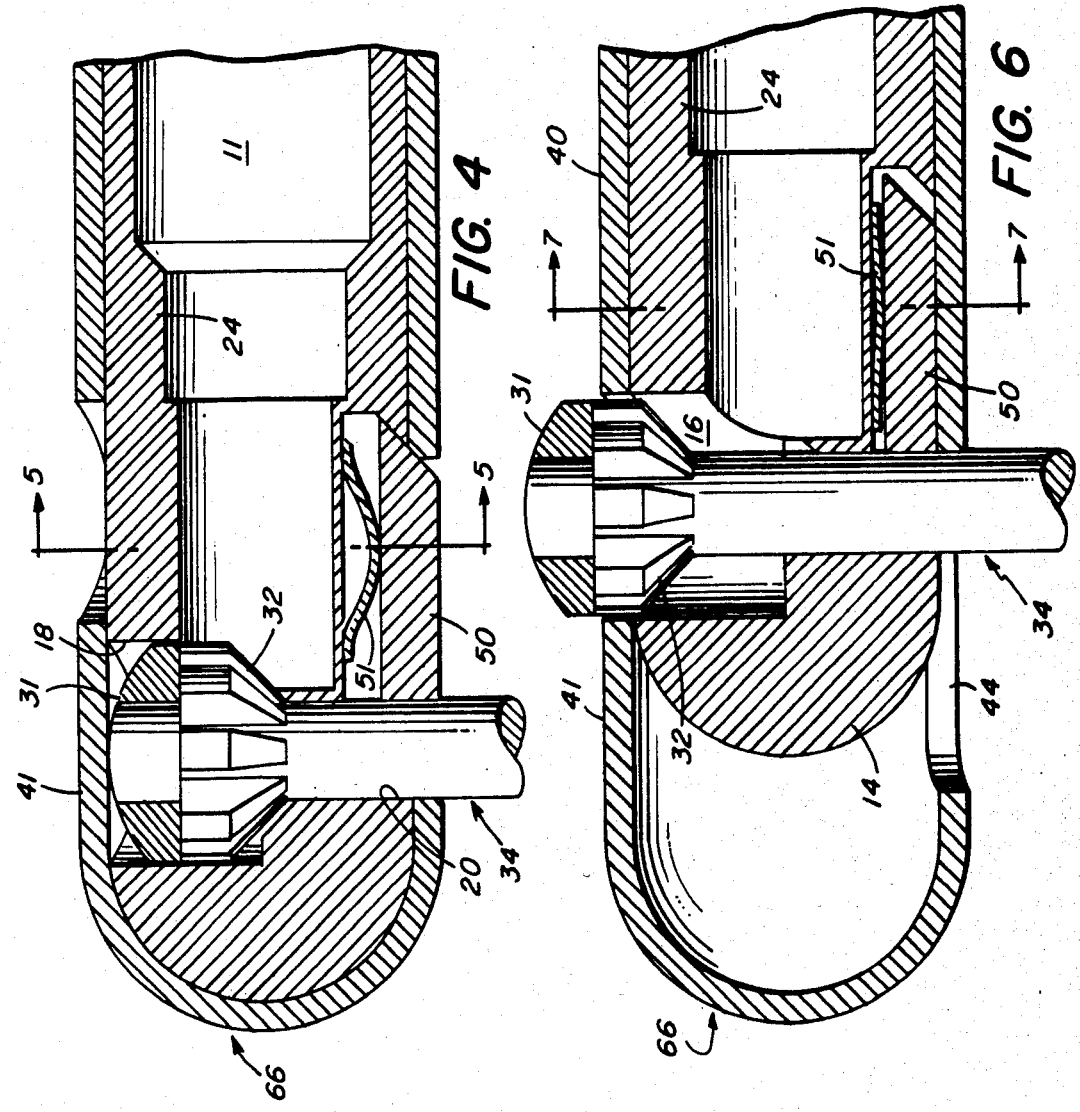
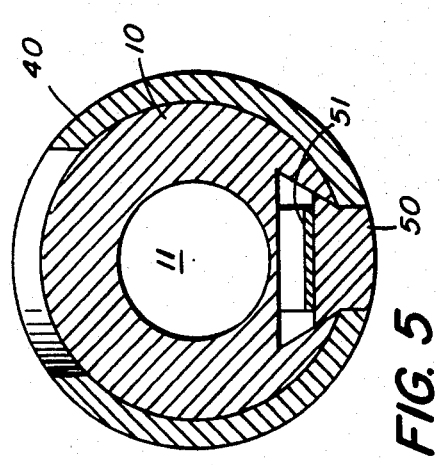
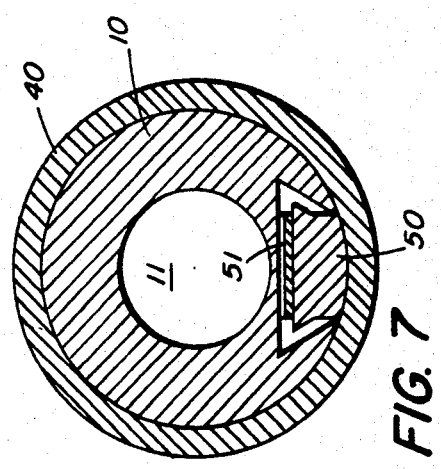

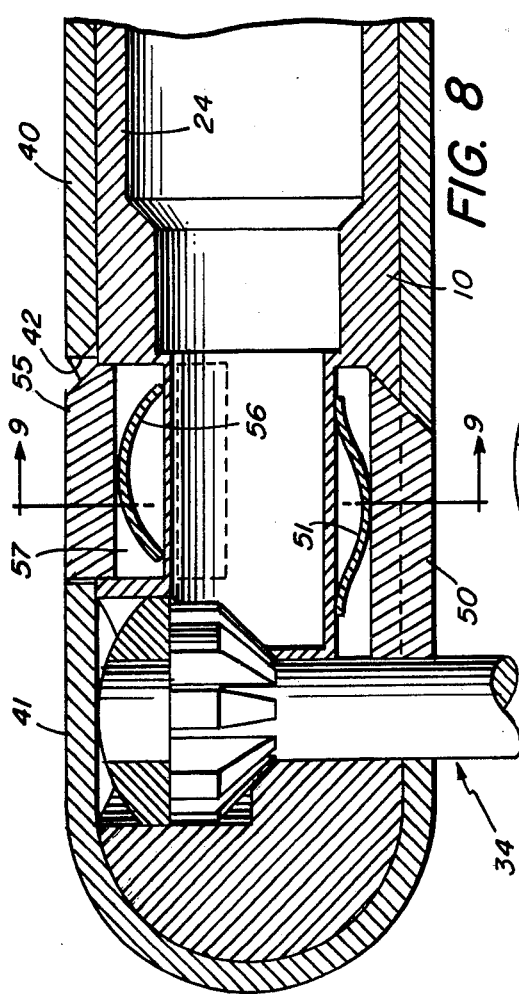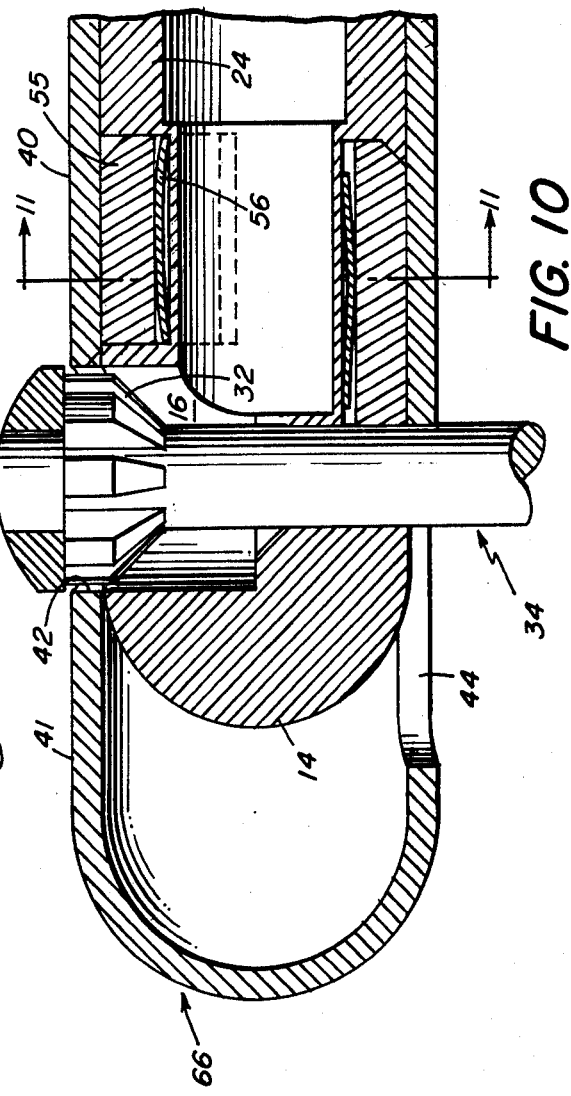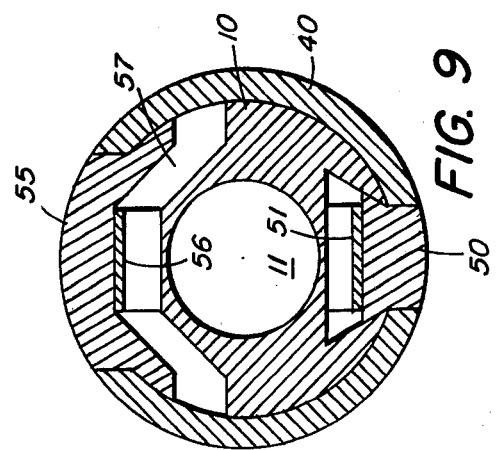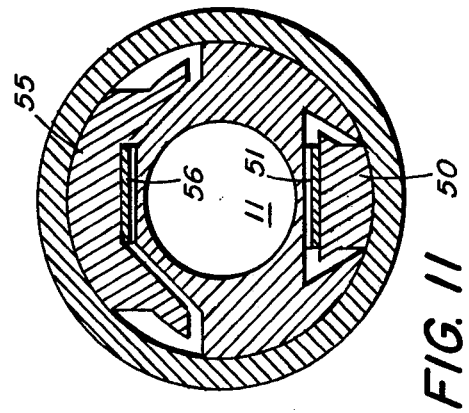

CONTRA-ANGLE HEAD FOR DENTISTRY

INTRODUCTION

This invention relates to a contra-angle head for dentistry which has a smooth exterior distinguished by absence of projecting parts (except, of course, the drill or other tool being used), and which can be made in small sizes.

BACKGROUND OF THE INVENTION

Those contra-angle heads intended for use by a dentist to drive interchangeably one or more of drills, burs, broaches, files and other tools used in dentistry incorporate rugged and usually precise mechanisms for accepting and locking the tools in place, driving them at desired speeds, and releasing them for removal quickly and reliably, but for the most part such contra-angle heads are bulky and large, have awkward shapes, and are heavy. The positions into which a dentist can put a tool in the mouth of a patient are restricted, and often a tool can be used to treat a patient only at the expense of great discomfort to the patient, and risk of harming surrounding tissue that is not directly involved in the procedure being undertaken.

Projecting parts, such as extending gear boxes and external latching levers, which are commonly found on contra-angle heads currently in use tend to aggravate such discomfort and risks. For example, in U.S. Pat. No. 3,369,298 a clutch is permanently rotatably fixed in a stub-housing oriented transversely to the principal housing, and gears to rotate the clutch on an axis transversely to the main drive shaft axis are housed in the stub housing, which is enlarged for that purpose. A tool can be removably inserted into the clutch from one end of the stub housing, and a lock lever is provided, externally, at the other end.

Attempts to provide smaller and smoother contra-angle heads with interchangeable tools have lead, in one instance, to a construction in which the tool is inserted through the stub housing from the locking end, and a threaded cap is provided at the same end to perform the locking function. As it is attempted to make a contra-angle head smaller, these parts, especially removable caps, become so small that they are easily lost, wasting the time of the dentist, and so expensive that their prices are difficult to justify in times of rising prices of other more important medical procedures.

THE PRIOR ART

My U.S. Pat. Nos. 4,268,252 and 4,285,671 and citations therein are the most pertinent prior art known to me.

GENERAL NATURE OF THE INVENTION

With this invention I provide a new contra-angle head that is rugged, safe and convenient to use, has a convenient latch mechanism which is devoid entirely of projections and extensions and which has a smooth outer surface surrounding the entire end of the head that is put into the mouth of a patient, can be made without angular contours, and while providing ready interchangeability of tools can be made smaller in size than prior contra-angle heads having similar operating features. My new contra-angle head can be used with a limitless variety of tools, as well as for prophylactic devices.

In my new contra-angle head, a rigid tubular housing, which can be made in one piece of any suitable material, such as metal or plastic, provides in one body elongated on the tubular axis two separate enclosures, one being an alley for a drive shaft and the other being a chamber for a dental tool, respectively, which rotate on axes that are angularly related. A tubular latch member closely envelopes substantially the entire housing, including the end enclosing the tool chamber, with a thin-walled cover having a smooth outer surface that is entirely devoid of projections, extensions, and angular surfaces. The chamber for a dental tool has at one end an access opening for receiving a dental tool in the chamber, and at the other end a smaller opening for passing and supporting a dental tool shaft. The latch member has a pair of diametrically-opposed openings, one the size of the access opening and the other a slot having width the same as the diameter of the smaller tool shaft opening. The latch member is movable on the housing to put it alternatively in a first location where the first latch opening is in register with the access opening and in a second location where a cover portion of the latch member overlies and covers the access opening. The slot is long enough and so oriented as to leave the tool shaft opening uncovered when the latch member is in each of said locations and in motion between them.

BRIEF DESCRIPTION OF THE DRAWINGS

FIG. 3 is an enlarged view showing details of the contra-angle of FIG. 1;

FIG. 4 is a longitudinal section of a modified contra-angle according to the invention;

FIG. 5 is a cross-section on line 5—5 of FIG. 4;

FIG. 6 shows FIG. 4 in the open-latch position;

FIG. 7 is a cross-section on line 7—7 of FIG. 6;

FIG. 8 is a longitudinal section of another modified contra-angle according to the invention;

FIG. 9 is a cross-section on line 9—9 of FIG. 8;

FIG. 10 shows FIG. 9 in the latch-open position; and

FIG. 11 is a cross-section on line 11—11 of FIG. 10.

DETAILED DESCRIPTION OF THE DRAWINGS

Figure 1:
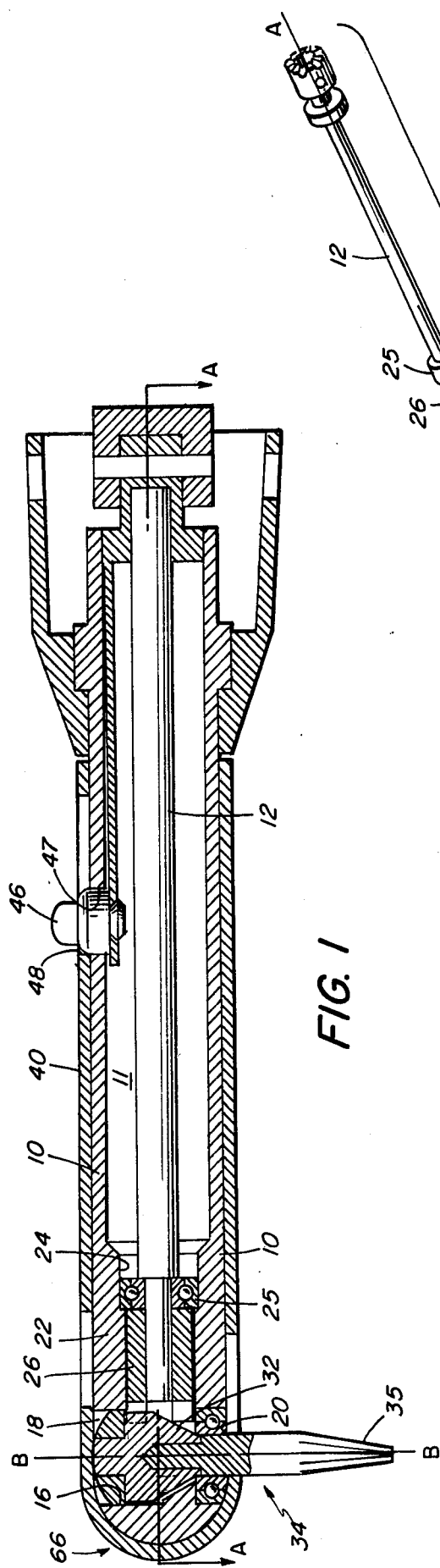
FIG. 1 is a longitudinal section through a contra-angle with a tool in place, according to the invention.
Figure 2:
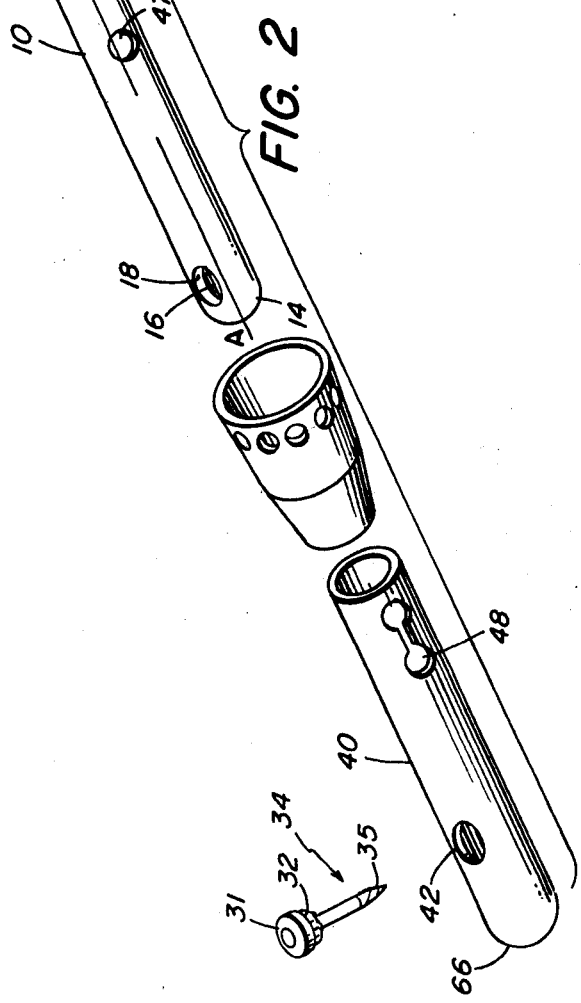
FIG. 2 is an exploded view of FIG. 1.

In FIGS. 1-3, inclusive, a principal tubular housing 10 provides a shaft alley 11 for enclosing a drive shaft 12 which is rotatable around the longitudinal axis A—A of the housing. The housing 10 has one end 14 rounded on the outside transversely to the axis A—A, and fitted with a tool chamber 16 having an access opening 18 into the housing at one side for receiving in said chamber a dental tool 34 for rotation on a tool axis B—B that is transverse to the housing axis A—A, said chamber 16 extending in the direction of the tool axis to the diametrically-opposite side of the housing having a tool shaft opening 20 through it, which latter opening may be in an anti-friction bearing 21 (FIG. 3). A transverse wall 22 between the tool chamber 16 and the shaft alley 11 has an aperture 24 on the housing axis A—A to provide support for an antifriction bearing 25 which is fitted to the shaft 12 at the end holding a coupling member 26, which has gear teeth 28 extending into the tool chamber 16 for engaging the mating teeth 32 of the tool 34 when the latter is present in the tool chamber, as is illustrated. In practice the contra-angle head will be fitted (at the right-hand end as seen in FIGS. 1 and 2) with means to couple it to a hand-piece, of which several varieties are in professional use. Such coupling means are not part of the invention, and are not further described. It will be understood that the shaft 12 is intended to be driven from the handpiece to which the contra-angle head is coupled.

The tool 34 may be similar in principle to the dental tool (30) which is described in U.S. Pat. No. 4,285,671, in that the gear teeth 32 of the present tool 34 are preferably adapted to engage easily with the driving gear teeth 28 when the tool is pushed into the tool chamber working end 35 first through the access opening 18 to and though the shaft opening 20, as is illustrated in and will be further described with reference to FIG. 6. The tool has a rounded head 31 at its wider gear end.

A latch member 40 in the form of a thin-walled tubular shell is coaxially fitted over the principal housing 10, covering the major portion of the principal housing and shaped to smoothly embrace the rounded end 14 of it. This essentially smooth covering for the entire "nose" end 66 of the contra-angle head is sanitary and safe to use; it has no projecting parts which might damage tissue in the mouth of a patient. The latch member has a first latch aperture 42 which is round and sized similar to the access opening 18 to the tool chamber, and a second elongated slot-like latch aperture 44 the width of which is approximately the same as the diameter of the tool shaft opening 20. The latch apertures 42 and 44 are located diametrically opposite each other in the shell 40, and are so positioned with relation to the openings 18 and 20 of the tool chamber 16 that when the shell is put in a first location on the principal housing 10 the first latch aperture 42 is in register with the access opening 18, and when the shell is in a second location on the principal housing a cover portion 41 of the shell overlies the access opening as is illustrated in FIG. 3. The slot-like latch aperture 44 overlies the tool shaft opening 20, and is long enough and so oriented as to leave the tool shaft opening uncovered when the shell 40 is in each of said locations and at all positions between them. A finger-latch 46,47 of known form carried by the principal housing 10, and cooperating with a dumb-bell shaped aperture 48 in the shell 40, serves to lock the latch member 40 in one or the other of the first and second locations. The latch member 40 is, in this embodiment of the invention, movable telescopically on the principal housing 10, between said two locations.

Operation of the invention, to install and remove tools, is illustrated in greater detail in FIGS. 4–7, next described. In those figures, parts like corresponding parts of FIGS. 1–3 bear the same reference characters. The shaft 12 and its parts are omitted, only to simplify the illustrations.

The embodiment of FIGS. 4–7 differs from that of FIGS. 1–3 in that the finger latch 46,47 and cooperating aperture 48 have been removed and a new latch consisting of a finger piece 50 and a leaf-spring 51 cooperating with the slot-like aperture 44 has been substituted. This not only simplifies the construction of the contra-angle; it also has the added virtue that the slot-like aperture 44 is filled with the finger piece 50 when a tool 34 is installed, as is seen in FIGS. 4 and 5.

Viewing FIGS. 6 and 7, when the finger piece 50 is pressed radially inward against the spring 51 the slot 44 is released so that the shell 40 can move to its first location in which the first latch aperture 42 is in register with the access opening 18. The tool 34 can then be removed from or inserted into the tool chamber, as is shown in FIG. 6. To lock a tool in place it is only necessary to push the rounded "nose" end 66 of the shell 40 to the second location in which the cover portion 41 overlies the access opening; in that location the rounded end 66 of the shell tightly embraces the rounded end 14 of the principal housing, and the finger piece 50 falls into the slot-like aperture 44 under urging of the spring 51, filling the "unused" portion of the slot-like aperture. This provides improved sanitation, as well as additional bearing surface for the shaft of the tool 34.

In FIGS. 8–11 a second latch consisting of a second finger piece 55 and spring 51 are fitted into a recess 57 in the principle housing 10 for cooperation with the first latch aperture 42. When a tool 34 is installed, as is seen in FIGS. 8 and 9, the second latch finger piece 55 extends into and fills the first latch aperture. This embodiment fills each of the latch apertures when the shell 40 is in the second location. The shell can be released, and moved to the first location, shown in FIGS. 10,11, by pressing the two finger-pieces 50,55 radially inward, toward each other.

I claim:

1. A contra-angle head for a dental handpiece comprising a rigid tubular housing member elongated on its axis to provide an alley open at a first end for receiving a drive shaft and having at the second end a chamber with an access opening though a side of said housing member for receiving in said chamber a dental tool for rotation on a tool axis that is transverse to said housing member axis, said chamber having a tool shaft opening through a diametrically-opposite side of said housing member from said access opening for passing a dental tool shaft, means in said tool shaft opening to support said dental tool shaft, when present, for rotation around said tool axis; a latch member in the form of a thin-walled tubular shell slidingly enclosing a portion of said housing member including said second end and being movable relative to said housing member, said latch member having a first latch aperture which is large enough to allow a tool to pass through said first access opening from outside said shell and a second elongated latch aperture the width of which is approximately the same as the diameter of said tool shaft opening, said latch apertures being located diametrically opposite each other in said shell, means for locating said latch member on said housing member and operative to put said latch member alternatively in a first location on said housing member in which said first latch aperture is in register with said access opening and in a second location on said housing member in which a cover portion of said shell overlies said access opening, said second latch aperture being long enough and so oriented as to leave said tool shaft opening uncovered when said latch member is in each of said locations and at all positions between them.

2. A contra-angle head according to claim 1 in which said access opening is larger than said tool shaft opening, for receiving and supporting in said chamber a tool having at one end of its shaft, remote from the working end, a gear head transversely larger than said tool shaft and fitted with a ring of driven gear teeth oriented toward said working end.

3. A contra-angle head according to claim 1 including said drive shaft in said alley carrying on its end confronting said chamber a ring of driving gear teeth projecting into said chamber, for driving a dental tool when present in said chamber, said access opening being larger than said tool shaft opening for receiving and supporting in said chamber a tool having at one end of its shaft, remote from the working end, a gear head transversely larger than said tool shaft and fitted with a ring of driven gear teeth oriented toward said working end for engaging said driving gear teeth when said tool is fitted into said chamber through said access opening with its working end passing out through said tool shaft opening.

4. A contra-angle head according to claim 3 in combination with a tool having a bearing surface on the end of said gear head remote from said working end, for engaging the inner surface of said cover portion of said shell so as to retain said tool in a working position when said latch member is in said second location.

5. A contra-angle head according to claim 1 including releasable means to lock said shell in said second location.

6. A contra-angle head according to claim 5 including spring-actuated lock means to fill at least one of said latch apertures when said shell is in said second location.

7. A contra-angle head according to claim 6 including two spring-actuated lock means to fill, respectively, each of said latch apertures when said shell is in said second location, said lock means being releasable by pressing said spring-actuated means toward each other.

* * * * *